(12) United States Patent
Sayama

(10) Patent No.: US 6,248,098 B1
(45) Date of Patent: Jun. 19, 2001

(54) DISPOSABLE DIAPER

(75) Inventor: Yasushi Sayama, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/168,833

(22) Filed: Oct. 8, 1998

(30) Foreign Application Priority Data

Oct. 8, 1997 (JP) .................................................. 9-276187

(51) Int. Cl.$^7$ ..................................................... A61F 13/15
(52) U.S. Cl. .............................. 604/385.28; 604/385.19; 604/385.27
(58) Field of Search ........................... 604/385.1, 385.2, 604/385.01, 385.19, 385.28, 385.27, 358, 381, 382, 384, 386, 387, 397, 398, 393

(56) References Cited

U.S. PATENT DOCUMENTS

| | | | |
|---|---|---|---|
| Re. 34,920 | * | 4/1995 | Aziz et al. ........................ 604/385.2 |
| 4,210,143 | * | 7/1980 | De Jonckheere .................... 128/287 |
| 4,681,579 | * | 7/1987 | Toussant et al. .................... 604/385 |
| 4,753,645 | * | 6/1988 | Johnson ............................. 604/378 |
| 4,808,178 | * | 2/1989 | Aziz et al. ........................ 604/385.2 |
| 4,909,803 | * | 3/1990 | Aziz et al. ........................ 604/385.2 |
| 4,990,147 | * | 2/1991 | Freeland ........................... 604/385.2 |
| 5,005,525 | * | 4/1991 | Stanton .................................. 119/95 |
| 5,032,121 | * | 7/1991 | Mokry ............................... 604/385.2 |
| 5,269,775 | * | 12/1993 | Freeland et al. ................... 604/385.5 |
| 5,304,159 | | 4/1994 | Tanji et al. . |
| 5,304,160 | * | 4/1994 | Igaue et al. ....................... 604/385.2 |
| 5,330,461 | * | 7/1994 | Leeker ............................. 604/385.2 |
| 5,342,342 | * | 8/1994 | Kitaoka ............................ 604/385.2 |
| 5,344,516 | * | 9/1994 | Tanji et al. ........................... 156/164 |
| 5,417,680 | * | 5/1995 | Kimura et al. .................... 604/385.2 |
| 5,520,674 | * | 5/1996 | Lavon et al. ...................... 604/385.1 |
| 5,567,265 | * | 10/1996 | Zajaczkowski ....................... 156/256 |
| 5,575,785 | * | 11/1996 | Gryskiewicz et al. ............. 604/385.2 |
| 5,576,091 | * | 11/1996 | Zajackowski et al. .............. 428/192 |
| 5,672,166 | * | 9/1997 | Vandemoortele ................... 604/385.2 |
| 5,674,213 | * | 10/1997 | Sauer ................................ 604/385.1 |
| 5,814,035 | * | 9/1998 | Gryskiewicz et al. ............ 604/385.1 |
| 5,843,067 | * | 12/1998 | Trombetta et al. ............... 601/385.2 |
| 5,904,674 | * | 5/1999 | Bonjour ............................ 604/385.2 |
| 5,913,851 | * | 6/1999 | Gryskiewicz et al. ............ 604/385.1 |
| 5,931,826 | * | 8/1999 | Faulks et al. ..................... 604/385.2 |
| 5,935,118 | * | 8/1999 | Gryskiewicz et al. ............ 604/385.1 |
| 5,957,906 | * | 9/1999 | Roe et al. ............................. 604/378 |
| 5,997,520 | * | 12/1999 | Ahr et al. .......................... 604/385.1 |
| 6,013,065 | * | 1/2000 | Suzuki et al. ..................... 604/385.2 |
| 6,017,336 | * | 1/2000 | Sauer ................................ 604/385.1 |
| 6,102,892 | * | 8/2000 | Putzer et al. ......................... 604/101 |
| 6,102,902 | * | 8/2000 | Jackson .............................. 604/387 |
| 6,103,952 | * | 8/2000 | Coles et al. .......................... 604/358 |
| 6,120,488 | * | 9/2000 | VanRijswijck et al. .......... 604/385.2 |
| 6,142,985 | * | 11/2000 | Feist ................................ 604/385.28 |
| 6,152,908 | * | 11/2000 | Widlund et al. ................. 604/385.19 |

FOREIGN PATENT DOCUMENTS

| | | |
|---|---|---|
| 0 631 767 | 1/1995 | (EP) . |
| 2 287 888 | 10/1995 | (GB) . |
| 2 294 398 | 5/1996 | (GB) . |
| 2 296 441 | 7/1996 | (GB) . |
| WO 97 39710 | 10/1997 | (WO) . |

* cited by examiner

Primary Examiner—Glenn K. Dawson
Assistant Examiner—Paul A. Shanoski
(74) Attorney, Agent, or Firm—Baker & Daniels

(57) ABSTRACT

A disposable diaper includes a main body and a supplemental member, the main body being formed on its inner surface in its transversely middle zone with a cavity adapted to receive excretion, for example, feces. The cavity is defined by a pair of side walls spaced apart from each other by a predetermined distance in the transversely middle zone of the main body and extending longitudinally of the main body, and a top wall extending between distal edges of the respective side walls. The top wall is formed with openings adapted to guide feces and urine, respectively, and elastic members are secured to the supplemental member in the proximity of upper edges of the respective side walls so as to be operatively associated with a crotch region of the diaper.

6 Claims, 3 Drawing Sheets

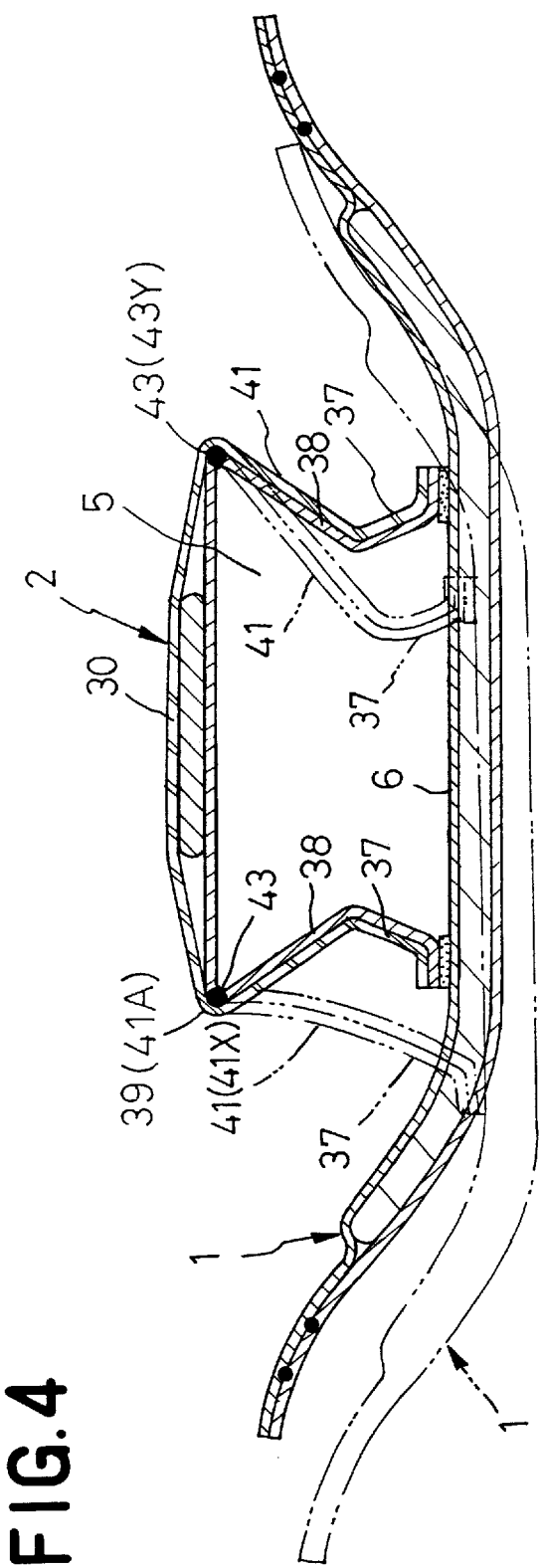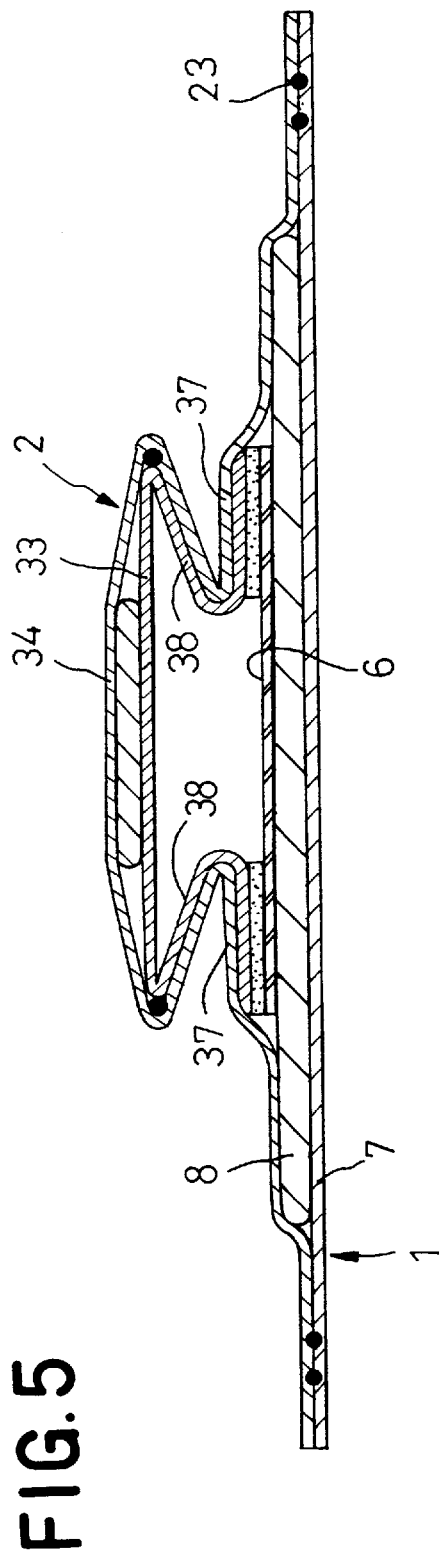

DISPOSABLE DIAPER

BACKGROUND OF THE INVENTION

This invention relates to disposable diapers and more particularly to disposable diapers having a cavity adapted to receive excretion.

Japanese Patent Application Disclosure Gazette (Kokai) No. Hei5-285174 discloses a disposable diaper comprising an opening formed in a topsheet lying inside the diaper in its transversely middle zone, a pair of flaps which extend laterally from transversely opposite side edges of the opening and elastic members provided along respective outer edges of the flaps. With this arrangement, the pair of flaps slope downward under the effect of the elastic members and facilitate excretion to flow into the opening.

With the above-mentioned diaper of prior art, the outer edges of the respective flaps are tightly placed against a wearer's body, for example, inguinal region and thereby a feces receiving pocket which is effective also to prevent excretion from leaking sideways. Even if the wearer's movement such as walking causes the diaper to shift in the wearer's crotch region, such movement will be absorbed by deformation of the flaps. Consequently, the flaps will have their outer side edges continuing to be tightly placed against the wearer's body substantially without formation of an undesirable gap which might cause body fluids to leak sideways. However, such effect can be obtained only when a movement of the diaper is as small as negligible since a sufficient contacting area is unavailable between the outer side edges and the wearer's skin. To ensure that the outer side edges of the flaps can be maintained in tight contact even when a movement of the diaper is relatively large, a stretching stress of the elastic members may be correspondingly increased. Such countermeasure, however, is inevitably limited because it may cause the elastic members to be uncomfortably pressed against the wearer's skin and create a feeling of discomfort against a wearer or even may adversely affect the normal blood circulation.

SUMMARY OF THE INVENTION

In view of the above problems, it is an object of the invention to provide an improvement such that, even when a movement of a diaper relative to the wearer's crotch region is relatively large, an opening of a pocket or a cavity adapted to receive and hold excretion such as feces can be reliably maintained in close contact with the wearer's skin without unacceptably shifting.

According to the invention, there is provided a disposable diaper having a longitudinal direction, a transverse direction, a front waist region, a rear waist region and a crotch region therebetween, the diaper comprising an main body and a supplemental member; the main body including a liquid-permeable topsheet, a liquid-impermeable backsheet and a liquid-absorbent core disposed therebetween; the supplemental member including a pair of side walls having proximal edges and distal edges and extending in the longitudinal direction and spaced apart from each other by a predetermined distance in the transverse direction, a top wall extending between the distal edges of the side walls, and a cavity defined by the side walls and the top wall; each of the side walls being bonded at the proximal edge onto the topsheet; the top wall being formed with an opening adapted to guide excretion into the cavity; and elastic members being secured to the supplemental member in the proximity of the distal edges of the side walls under appropriate tension so that the elastic members normally bias the side walls to rise up on the topsheet and simultaneously bias the top wall to be spaced apart from the topsheet.

According to a preferred embodiment of this invention, the top wall is formed with a pair of openings adapted to guide feces and urine of excretion separately.

According to another preferred embodiment of this invention, the leakage-proof walls as well as the top wall are made of hydrophobic sheets.

BRIEF DESCRIPTION OF THE DRAWINGS

FIG. 4 is a view similar to FIG. 2 but illustrating the diaper as in its curved state; and FIG. 5 is a view similar to FIG. 2 but illustrating an alternative embodiment of the invention.

DESCRIPTION OF THE PREFERRED EMBODIMENTS

Details of a disposable diaper provided according to the invention will be more fully understood from the following description made with reference to the accompanying drawings.

Figure 1:
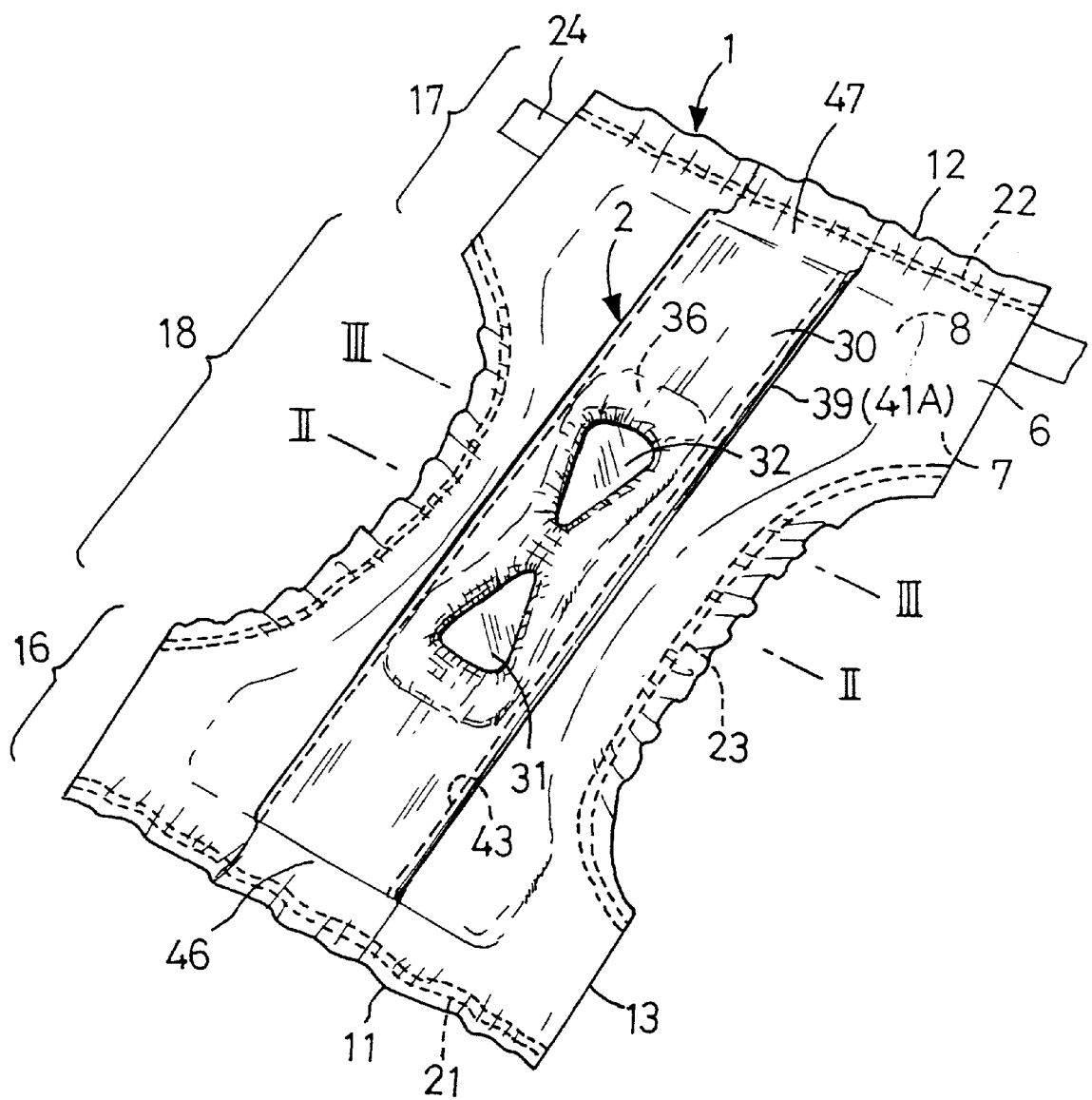
FIG. 1 is a perspective view illustrating an embodiment of a disposable diaper according to the invention.
Figure 2:
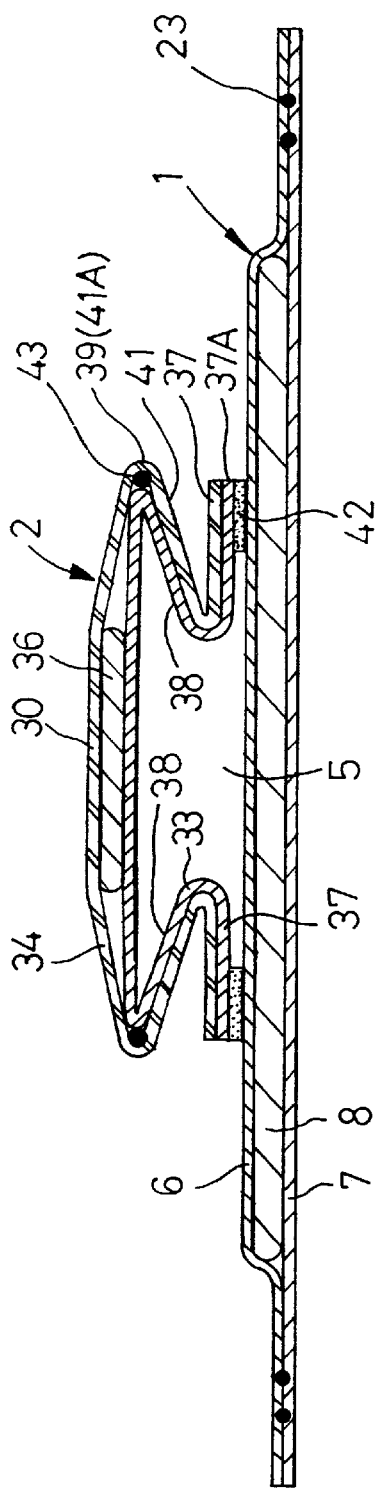
FIG. 2 is a sectional view taken along a line II—II in FIG. 1.

FIGS. 1 and 2 illustrate an embodiment of a disposable diaper according to the invention respectively in a perspective view and in a sectional view taken along a line II—II in FIG. 1. The diaper comprises a main body 1 serving to absorb and to contain body fluids and a supplemental member 2 lying on a top surface of the main body 1 so as to form together with the main body 1 a cavity 5 adapted to trap excrement.

The main body 1 includes a liquid-permeable topsheet 6, a liquid-impermeable backsheet 7 and a liquid-absorbent core 8 disposed between these two sheets 6, 7. These sheets 6, 7 are placed one upon another and bonded together by means of hot melt adhesive (not shown) along their portions extending outward beyond peripheral edges of the core 8. As a whole, the main body 1 presents a shape of hour-glass. Such hour-glass-shaped main body 1 is defined by longitudinally opposite ends 11, 12 and transversely opposite side edges 13, 13. As viewed longitudinally, the main body 1 has a front waist region 16, a rear waist region 17 and a crotch region 18 extending between these front and rear waist regions 16, 17. In the crotch region 18, the side edges 13, 13 are inwardly curved so as to extend around the wearer's legs when the diaper is actually put on the wearer's body.

Adjacent the longitudinally opposite ends 11, 12, elastic members 21, 22 are bonded under appropriate tension to an inner surface of at least one of the topsheet 6 and the backsheet 7 so as to extend circumferentially of the diaper. Also adjacent the side edges 13 in the crotch region 18, elastic members 23 are bonded under appropriate tension to the inner surface of at least one of the topsheet 6 and the backsheet 7 so as to extend around the wearer's legs when the diaper is actually put on the wearer's body. In the rear waist region 17, a pair of tape fasteners 24 extend laterally from the respective side edges 13.

The supplemental member 2 lies on the top surface of the main body 1 and longitudinally extends along a transversely middle zone of the main body 1. The supplemental member 2 includes a top wall 30 which is formed with a first opening 31 and a second opening 32. Locations of these first and second openings 31, 32 are selected so that the first and second openings 31, 32 are substantially centered with the wearer's urinary organs and anus, respectively. As will be apparent from FIG. 2, the supplemental member 2 includes inner and outer sheets 33, 34 placed one upon another and integrated by means of hot melt adhesive (not shown) as well as a absorbent pad member 36 disposed between these inner and outer sheets 33, 34 along peripheral edges of the first and second openings 31, 32. Transversely opposite side portions of the inner and outer sheets 33, 34 are folded in Z- and inverted Z-shapes. With the supplemental member 2, any one of the first and second openings 31, 32 may be eliminated or these two openings 31, 32 may be combined into a single larger opening, if desired.

With the inner and outer sheets 33, 34 having been folded in the manner as described above, the supplemental member 2 is defined by the top wall 30 and transversely opposite side walls 41, 41 consisting of lower portions 37 and upper portions 38 extending outward from the lower portions 37 to side edges 39 of the top wall 30. The side edges 39 correspond to distal edges 41A of the respective side walls 41. According to this embodiment, the respective lower portions 37 are bonded at least over their partial widths along their proximal edges 37A to the topsheet 6 by means of hot melt adhesive 42. Obviously, it is also possible to bond the lower portions 37 to the topsheet 6 over their full widths. The respective side walls 37 are spaced apart from each other by a predetermined distance. Adjacent the respective distal edges 41A of the side walls 41, i.e., adjacent the respective side edges 39 of the top wall 30, there are provided elastic members 43 associated with the crotch region 18. These elastic members 43 extend longitudinally of the diaper and are secured under appropriate tension to an inner surface of at least one of the inner and outer sheets 33, 34. At longitudinally opposite ends 46, 47 (See FIG. 1) of the supplemental member 2, the top wall 30, the lower portions 37 and the upper portion 38 are placed one upon another and bonded together, on one hand, and bonded to the main body 1 in the proximity of the longitudinally opposite ends 11, 12 of the main body 1, on the other hand, by means of adhesive (not shown). While the top wall 30 is shown as spaced apart upward from the topsheet 6 of the main body 1 in order to facilitate a sectional construction of the diaper to be understood, the top wall 30 actually lies closely adjacent to or even in contact with the main body 1.

Figure 3:
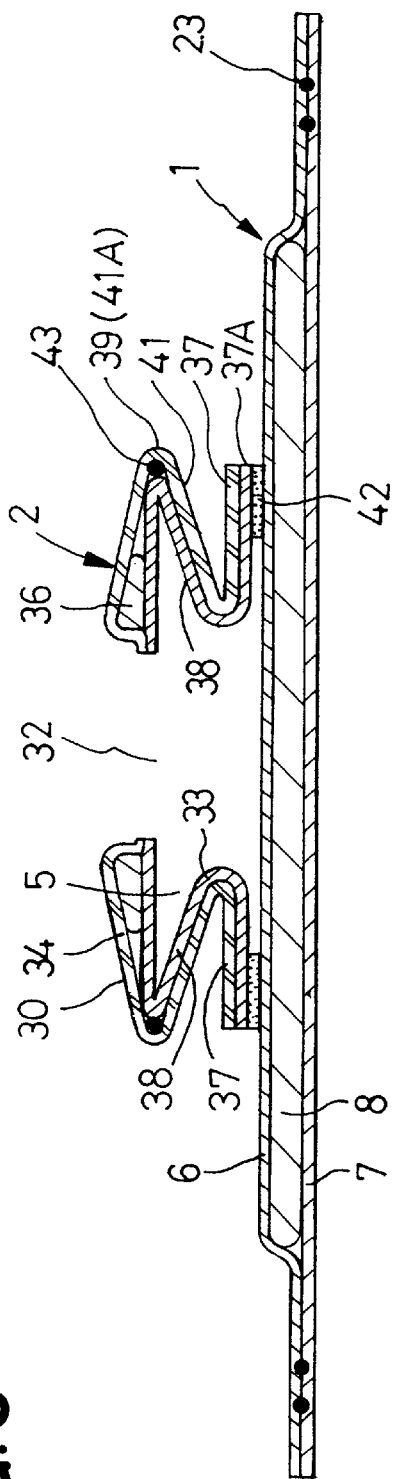
FIG. 3 is a sectional view taken along a line III—III in FIG. 1.

FIG. 3 is a sectional view taken along a line III—III in FIG. 1. The second opening 32 is formed in a transversely middle zone of the top wall 30 and, along an peripheral edge of the second opening 32, the inner and outer sheets 33, 34 are bonded together using adhesive or heat-sealing technique. The absorbent pad 36 extends around the second opening 32. The first opening 31 presents its sectional configuration similar to that of the second opening 32.

FIG. 4 is a view similar to FIG. 2 but illustrating the diaper put on the wearer's body (not illustrated). As the diaper is put on the wearer's body, the diaper is curved with the topsheet 6 lying inside, not only as viewed longitudinally but also as viewed transversely of the diaper. With the diaper curved in this manner, the elastic members 43 associated with the crotch region 18 contract and cause the free remainders, if any, of the respective lower portions 37 as well as the respective upper portions 38 to rise up on the inner surface, i.e., the topsheet 6 of the main body 1. Consequently, the top wall 30 is spaced apart upward from the inner surface of the main body 1. In this way, the cavity 5 defined by the main body 1 and the supplemental member 2 so as to receive both feces and urine has its inner volume enlarged to the maximum. Thereupon, the top wall 30 including the portions of the side walls 41 extending in the proximity of their distal edges 41A are tightly placed against the wearer's crotch region.

Imaginary lines in FIG. 4 exemplarily indicate respective positions occupied by the main body 1 and the supplemental member 2 when the diaper has laterally shifted relatively to the wearer's crotch region. With the diaper of well known art, substantially no change occurs in the relative position of the main body 1 and the supplemental member 2 so far as the diaper shifts together with the wearer's crotch region. However, when the diaper shifts independently of the wearer's crotch region, an undesirable change may occur in the foresaid relative position so that, for example, the diaper may get out of the wearer's urinary organs and anus. In this regard, the invention provides a unique arrangement such that the part of the diaper intended to come in contact with the wearer's crotch region particularly around urinary organs and anus is limited to the top wall 30 including the portions of the upper portions 38 extending in the proximity of their distal edges 41A. Such part of the supplemental member 2 is connected by the relatively deformable upper portions 38 to the main body 1. With such an arrangement, shift or movement of the main body 1 is absorbed in the form of corresponding shift or movement of the side walls 41 and substantially not transmitted to the top wall 30. Even when a movement of the main body 1 pulls one of the side walls 41, for example, the side wall 41X leftward as viewed in FIG. 4, the top wall 30 is maintained in tight contact with the wearer's body under the effect of the elastic members 43 extending along the distal edges 39 of the side walls 41 so as to operate in association with the crotch region 18. In addition, a frictional force generated between the top wall 30 itself and the wearer's body against which the top wall 30 is tightly placed is effective to reduce a tensile strength transmitted from the side wall 41X via the top wall 30 to one of the elastic members, for example, the elastic member 43Y. This makes a movement of the top wall 30 further difficult.

FIG. 5 is a view similar to FIG. 2 but illustrating an alternative embodiment of the invention. According to this alternative embodiment, the main body 1 comprises a liquid-absorbent core 8, a liquid-permeable topsheet 6 extending between longitudinally opposite ends of the core 8 and a liquid-impermeable backsheet 7 extending outward beyond peripheral edges of the core 8. The inner sheet 33 of the supplemental member 2 has its outer side edges 33 substantially in coincidence with outer side edges of the topsheet 6. The outer sheet 34 extends outward beyond the peripheral edges of the core 8 so as to be placed upon and bonded to the backsheet 7. The topsheet 6 and the backsheet 7 may be selectively bonded or not bonded to the core 8 by means of adhesive. The elastic members 23 intended to surround the wearer's legs are secured to the inner surface of at least one of said backsheet 7 and the outer sheet 34.

According to the invention, a nonwoven fabric or porous plastic sheet may be used as material for the topsheet 6 and such material may be suitably treated to make it hydrophilic prior to its use. A plastic sheet or such plastic sheet laminated with nonwoven fabric may be used as material for the backsheet 7. Fluffy pulp or a mixture of such fluffy pulp and polymer powder of high absorptivity may be used as material for the core 8. Of the inner and outer sheets 33, 34, at least the outer sheet 34 is preferably made of a hydrophobic sheet, more preferably, of hydrophobic and liquid-impermeable sheet. The inner sheet 33 may be made of a hydrophilic sheet, if necessary. The absorbent pad 36 may be made of natural fibers such as fluffy pulp or cotton, synthetic fibers, preferably crimped synthetic fibers, or a soft foam plastic sheet such as urethane foam sheet.

The cavity to receive excretion, the most important feature of the diaper according to the invention, is normally biased by the elastic members associated with the crotch region to rise up on the inner surface of the main body. The cavity includes transversely opposite side walls having a relatively high freedom of movement and the top wall extending the distal edges of the respective side walls so as to be tightly placed against the wearer's crotch region particularly around the wearer's urinary organs and anus. Such feature ensures that the top wall does not readily get out of its normal position properly covering the urinary organs and anus and therefore the cavity can reliably catch excretion even if the diaper shifts independently of the wearer's body.

What is claimed is:

1. A disposable diaper having a front waist region, a crotch region, and a rear waist region extending in a longitudinal direction, the diaper comprising a main body and a supplemental member;

the main body including a liquid-permeable topsheet, a liquid-permeable backsheet and a liquid-absorbent core disposed therebetween;

the supplemental member being made from components which are separate from components from which the main body is made, the supplemental member including a pair of side walls having proximal edges and distal edges and extending in the longitudinal direction and spaced apart from each other by a predetermined distance in a transverse direction, a top wall extending between the distal edges of the side walls, and a cavity defined between the side walls and beneath the top wall;

each of the side walls being folded in a sidewise V-shaped along a folding line that extends in the longitudinal direction of the side walls between the proximal and distal edges and being bonded at discrete portions, at the proximal edges to the topsheet above a region of the liquid-absorbent core; without extending over the sides of said core the top wall being provided with an opening which is adapted to guide excretion into the cavity; and elastic members being secured to the supplemental member in the proximity of the distal edges of the side walls under tension so that the elastic members normally bias the side walls to rise up on the topsheet and simultaneously bias the top wall to be spaced apart from the topsheet.

2. The diaper according to claim 1, wherein the top wall is formed with a pair of openings adapted to separately guide feces and urine into the cavity.

3. The diaper according to claim 1, wherein the side walls and the top wall are made of hydrophobic materials.

4. The diaper according to claim 2, wherein an absorbent pad extends around the openings.

5. The diaper according to claim 1, wherein the supplemental member includes an inner sheet and an outer sheet bonded to the inner sheet.

6. A disposable diaper having a front waist region, a crotch region, and a rear waist region extending in a longitudinal direction, the diaper comprising a main body and a supplemental member;

the main body including a liquid-permeable topsheet, a liquid-impermeable backsheet and a liquid-absorbent core disposed therebetween, the crotch region being inwardly curved at transverse side edges thereof, elastic members being secured to the main body along longitudinally opposite ends thereof and along curved edges of the crotch region;

the supplemental member being made from components which are separate from components from which the main body is made, the supplemental member including a pair of side walls having proximal edges and distal edges and extending in the longitudinal direction and spaced apart from each other by a predetermined distance in a transverse direction, a top wall extending between the distal edges of the side walls, and a cavity defined between the side walls and beneath the top wall;

each of the side walls being folded in a sidewise V-shape along a folding line that extends in the longitudinal direction of the side walls between the proximal and distal edges and being bonded at discrete portions at the proximal edges to the topsheet above a region of the liquid-absorbent core without extending over the sides of said core, without extending over the sides of said core;

the top wall being provided with an opening which is adapted to guide excretion into the cavity; and elastic members being secured to the supplemental member in the proximity of the distal edges of the side walls under tension so that the elastic members normally bias the side walls to rise up on the topsheet and simultaneously bias the top wall to be spaced apart from the topsheet.

* * * * *